United States Patent [19]

Tonedachi et al.

[11] 4,287,221

[45] Sep. 1, 1981

[54] METHOD FOR PROVIDING ENTERIC COATING ON SOLID DOSAGE FORMS

[75] Inventors: Masayuki Tonedachi, Tokyo; Fujio Sekigawa, Omiya; Katsuyoshi Minemura, Ageo, all of Japan

[73] Assignee: Shin-Etsu Chemical Co., Ltd., Tokyo, Japan

[21] Appl. No.: 109,117

[22] Filed: Jan. 2, 1980

[30] Foreign Application Priority Data

Jan. 16, 1979 [JP] Japan .................................... 54-4114

[51] Int. Cl.$^3$ .............................................. A61K 9/32
[52] U.S. Cl. ......................................... 427/3; 424/35
[58] Field of Search ............................. 424/35; 427/3; 106/197 R; 536/66

[56] References Cited

U.S. PATENT DOCUMENTS 2,843,583  7/1958  Voris ....................................... 536/66
3,935,326  1/1976  Groppenbacker ..................... 424/35

*Primary Examiner*—Sam Silverberg
*Attorney, Agent, or Firm*—Toren, McGeady and Stanger

[57] ABSTRACT

The invention provides a novel method for providing entric coating on solid dosage forms using an aqueous coating liquid so that the problems inherent to the use of a coating liquid in an organic solvent can completely be eliminated. The inventive method comprises dispersing a finely divided powder of a hydroxypropylmethylcellulose phthalate in an aqueous medium containing triacetin to give an aqueous coating liquid with which the solid dosage forms are coated, for example, by spraying and dried. It is necessary that the preparation of the coating liquid and the coating procedure with the coating liquid are performed throughout while keeping the temperature of the liquid below 25° C. so as that the particles of the hydroxypropylmethylcellulose phthalate are not dissolved in the medium forming a stable dispersion without adhesive coalescence.

4 Claims, No Drawings

METHOD FOR PROVIDING ENTERIC COATING ON SOLID DOSAGE FORMS

BACKGROUND OF THE INVENTION

The present invention relates to a method for providing enteric or enterosoluble coating on solid dosage forms or, more particularly, to a method for providing enteric coating on solid dosage forms by use of an aqueous coating liquid.

As is well known, enteric-coated solid dosage forms are in general prepared by use of a coating solution or liquid with an organic solvent as the solvent or dispersing medium. The use of such an organic coating liquid is sometimes undesirable since the use of large amounts of organic solvents always involves problems of a danger of explosion or fire hazards and a health problem of workers if not to mention the increased cost inherent to the solvent per se as well as the cost caused by the investment for the facilities for the recovery of the solvent or prevention of air and sewage pollution by the organic solvent.

It has been therefore a long-desired problem to be solved in the pharmaceutical technology to develop a method for providing enteric coating on solid dosage forms by not using a coating liquid with an organic solvent. Various attempts have been made in this direction according to which a finely divided coating material is dispersed or suspended in a medium of water or a mixed solvent of water as the main component and ethyl alcohol to give a coating liquid.

One of the problems in the use of an aqueous coating liquid is that addition of certain kinds of additives such as a stabilizing agent and an auxiliary solvent is indispensable in order to improve the stability of the coating liquid while these additives canot be free from the problem of their own toxicity, especially, when they remain in the coating layer on the entericcoated solid dosage forms. Thus no satisfactory method has yet been established in which the above described problems in the prior art are completely solved.

SUMMARY OF THE INVENTION

An object of the present invention is therefore to provide a novel method for providing enteric coating on solid dosage forms by not using a coating liquid with an organic solvent as the medium so that the problems inherent to the use of an organic solvent are completely eliminated also without the drawbacks in the prior art method using an aqueous coating liquid.

The inventors have conducted extensive investigations on the above given technical problems and arrived at a discovery that satisfactory enteric coating can be formed by use of an aqueous coating liquid prepared by dispersing a hydroxypropylmethylcellulose phthalate (abbreviated as HPMCP hereinafter), which is a known enterosoluble coating material, in an aqueous dispersing medium containing triacetin as a plasticizer for the HPMCP to improve the film-forming property thereof. It has been unexpectedly discovered that the advantages of the invention are obtained only when the procedure of the preparation of the coating liquid as well as the procedure of coating are carried out under adequate temperature control even without the use of other kinds of suspending agents or other additives.

Thus, the method of the present invention for providing enteric coating on solid dosage forms comprises (a) dispersing a HPMCP having an average particle diameter not exceeding 100 μm in water containing triacetin at a temperature of 25° C. or below to form an aqueous coating liquid, (b) spraying the thus prepared coating liquid on to the surface of a solid dosage form while the coating liquid is kept at a temperature of 25° C. or below to form a coating layer, thereon and (c) drying the thus coated solid dosage form.

DETAILED DESCRIPTION OF THE PREFERRED EMBODIMENTS

The coating material used in the present invention is a HPMCP which is cnventionally used for providing enteric coating on solid dosage forms. It is, however, necessary that the HPMCP used in the present invention should have an average particle diameter of not exceeding 100 μm. This is because a HPMCP of coarser particles than 100 μm cannot give a stable dispersion in the aqueous dispersion medium. In addition, an aqueous dispersion containing such large particles of HPMCP may cause jamming of the nozzle of a spray gun used in the coating procedure and the coating film formed on the solid dosage form is sometimes inferior in smoothness due to the presence of coarser particles.

The dispersion medium for the aqueous coating liquid in the present invention is water containing triacetin. The physiological safety of triacetin is well established in the pharmaceutical technology and commercially available triacetin of any grade can be used satisfactorily in most cases without further purification.

To describe the procedure for the preparation of the coating liquid, a weighed amount of the HPMCP is merely added and dispersed under agitation in water containing desired amount of triacetin. It is of course optional that a master dispersion containing the HPMCP in high content prepared in advance is diluted by adding water containing triacetin. It is necessary in this procedure that the aqueous dispersion medium is maintained throughout at a temperature of 25° C. or below or, preferably, 20° C. or below. When the temperature of the aqueous dispersion medium is higher than 25° C. or, rather, when the aqueous dispersion of the HPMCP is kept at a temperature exceeding 25° C. for an unduly long time, the HPMCP is partly dissolved in the medium so that the resultant coating liquid has no desired property in addition to the problem of possible jamming of the spray nozzles.

The amount of the HPMCP to be dispersed in the aqueous medium is desirably such that the content of the HPMCP in the finished coating liquid is in the range from 3 to 20% by weight or, more preferably, from 5 to 15% by weight. When the content of the HPMCP is lower than the above range, an economical disadvantage is caused by the unduly long time taken for providing a coating film of desired thickness while higher contents of the HPMCP in the coating liquid result in inferior smoothness of the finished coating film obtained therewith.

The triacetin admixed in the aqueous dispersion medium serves as a kind of plasticizer to improve film formation of the HPMCP on the solid dosage form when the particles of the HPMCP in the wet coating layer are dried on the surface with heat. In this respect, the amount of triacetin in the coating liquid is determined in relation to the amount of the HPMCP and it is preferable that the amount of triacetin in the coating liquid is in the range from 5 to 50% by weight or, more preferably, from 10 to 40% by weight based on the amount of the HPMCP in the coating liquid. When the amount of triacetin is relatively large, the film of the HPMCP is rich in pliability by the plasticizing effect of triacetin so that an advantage is obtained in coating solid dosage forms of complicated forms. The use of a relatively large amount of triacetin is not detrimental in the enterosolubility and in the resistance against antigastric juice of the coating films obtained with the coating liquid.

It is of course optional that the coating liquid is further admixed with conventional additives such as coloring agents, e.g. dyes and pigments, and flavorings or sweetenings.

The solid dosage forms to be coated in accordance with the method of the invention include tablets, pills, granules, capsules and the like and the coating process is performed in a conventional manner using a pan coater, drum-type coater, fluidizing coater or other suitable coating machines.

It is recommendable that the coating liquid is agitated continuously during the procedure of coating in order to prevent settling of the HPMCP and other solid ingredients, e.g. pigments, contained in the coating liquid. The coating liquid is also desirably kept at a temperature of 25° C. or below during its storage in a tank as well as on the way to the spray gun from the storage tank through piping since the elevation of the temperature of the coating liquid above 25° C. may cause adhesive coalescence of the particles of the HPMCP leading to the jamming of the spray nozzle or rugged surface condition of the finished coated solid dosage forms. In this connection, it is undesirable that the coating liquid being transferred from the storage tank to the spray gun undergoes an excessive shearing force as in an unduly narrow or constricted piping wich may lead to the temperature elevation of the coating liquid causing clogging of the particles of the HPMCP on to the inner walls of the piping. Therefore, it is recommendable to provide jackets around the storage tank and the piping from the tank to the spray gun of the coating machine through which a cooling medium is passed to prevent temperature elevation of the coating liquid.

The procedure of coating per se is performed in a conventional manner using the above mentioned coating machine. In carrying out coating, it is recommended that the surface temperature of the solid dosage forms under coating is maintained in the range from 25° C. to 55° C. by appropriately controlling or balancing the feeding rate of the coating liquid and the flow rate and temperature of the air supply for drying. When the surface temperature of the solid dosage forms under coating is outside the above range, certain problems may arise such as a decreased taking up of the HPMCP utilized for film formation on the solid dosage forms or decreased resistance of the coating films against gastric juice.

The thickness of the enteric coating layer in the inventive method is usually in the range from 0.01 to 0.20 mm to ensure satisfactory entero-solubility.

After completion of coating with the coating liquid and drying in the manner as described above, the coated solid dosage forms are, if desired, subjected to polishing by use of a wax, sugar coating or over-coating with another coating material.

It is of course optional that the solid dosage forms are, prior to the coating in accordance with the inventive method, provided with an undercoating with a hydroxypropylmethlcellulose or other suitable coating materials so as that the inventive method be safely applicable even to those solid dosage forms liable to chipping off or breaking giving excellent enteric-coated dosage forms with high resistance against gastric juice. This undercoating is of significance, in particular, to overcome a disadvantage in the inventive method that the infiltration of the aqueous medium in the disage forms increases the loss by breaking or chipping off due to the relatively low viscosity of the coating liquid in the invention in comparison with conventional viscous coating liquids or solutions.

In the following, the method of the present invention is described in further detail by way of examples.

EXAMPLE 1

A commercially available HPMCP (HP-55, a product by ShinEtsu Chemical Co., Japan) was further subjected to pulverization into a finely divided powder having an average particle diameter of about 10 μm and a maximum particle diameter of 30 μm.

Into a mixed dispersion medium composed of 5200 g of water and 180 g of triacetin dissolved therein was added 600 g of the above prepared finely divided powder of HPMCP with agitation while the temperature of the dispersion medium was kept at 20° C. followed by further agitation for 5 minutes to give a coating liquid.

Tablets for simulation having a diameter of 9 mm and each weighing 280 mg were prepared with lactose and starch and 10 kg of the tablets were subjected to coating with the above prepared coating liquid in a 24-inch Accela-coater which was a drum-type coating machine equipped with a constant rate pump made by Tokyo Rika Kikai Co., Japan and a spray gun with a nozzle of 1.2 mm diameter made by Freund Industrial Co., Japan. The coating liquid was continuously agitated throughout the coating procedure. The conditions for coating were as follows.

Temperature of the coating liquid: 20° C.
Rate of supply of coating liquid: 55 g/minute
Temperature of air for drying: 90° C.
Flow rate of air for drying: 4 m³/minute
Flow rate of air for spraying: 150 liters/minute
Temperature of tablets: 35°–40° C.
Time for coating: 110 minutes The above obtained coated tablets had a coating of about 20 mg per tablet which corresponded to about 0.11 mm thickness of the coating layer.

The coated tablets were subjected to the disintegration test for enteric-coated solid dosage forms according to the method specified in the Ninth Revised Japanese Pharmacopoeia with the first and the second solutions to find that the tablets remained unchanged during the test time in the first solution while the disintegration time in the second solution was 15 to 16 minutes.

The above described coating procedure was repeated in the same manner except that the coating liquid in the storage tank was kept at a temperature of 10° C. or 15° C. instead of 20° C. The results were as satisfactory as in the above test without any troubles.

For comparison, the coating test was performed with the same coating liquid kept at 30° C., the other conditions being the same as in the above. In this case, the piping from the storage tank of the coating liquid to the spray gun and the nozzle of the spray gun were frequently plugged up by the clogging particles of the HPMCP so that the coating operation must be discontinued for cleaning of them. In addition, the coating liquid became coagulated after about 60 minutes from its preparation so that coating could no longer be continued.

When the temperature of the coating liquid was further increased to 40° C., the coating liquid was coagulated already before beginning of the coating operation so that no coated tablets were obtained.

EXAMPLE 2

A coating liquid was prepared at 20° C. in a similar manner to Example 1 from 210 g of the same finely divided powder of the HPMCP, 53 g of triacetin, 3 g of a food dye Red No. 2 and 1840 g of water and 3 kg of soft-gelatine capsules were subjected to coating in a Glatt fluidized-coating machine with the coating liquid to give a coating of 55 mg per capsule which corresponded to a thickness of 0.13 mm of the coating layer. The coating liquid was agitated continuously during the coating procedure. The conditions for the coating procedure were as follows.

Temperature of coating liquid: 20° C.
Rate of supply of coating liquid: 40 g/minute
Temperature of fluidizing air: 40°-45° C.
Temperature of exhaust air: 35° C.
Time for coating: 55 minutes The coated capsules were subjected to the disintegration test to find that no disintegration took place in the first solution during the test time while the disintegration time in the second solution was 11–13 minutes.

What is claimed is:

1. A method for providing an enteric coating on a solid dosage from which comprises
   (a) dispersing a hydroxpropylmethylcellulose phtalate having an average particle diameter not exceeding 100 μm in water containing triacetin amount from 5% to 50% by weight based on the amount of the hydroxypropylmethylcellulose phthalate at a temperature of 25° C. or below to form an aqueous coating liquid,
   (b) spraying the thus prepared coating liquid on to the surface of the solid dosage form while the coating liquid is kept at a temperature of 25° C. or below to form a coating layer thereon, and
   (c) drying the thus coated solid dosage form.

2. The method for providing enteric coating on a solid dosage form as claimed in claim 1 wherein the thickness of the coating film is in the range from 0.01 mm to 0.20 mm.

3. The method for providing enteric coating on a solid dosage form as claimed in claim 1 wherein the solid dosage form is provided with an undercoating prior to the step (b) in claim 1.

4. The method for providing enteric coating on a solid dosage form as claimed in claim 3 wherein the undercoating is provided with a hydroxypropylmethylcellulose.

* * * * *

UNITED STATES PATENT OFFICE
CERTIFICATE OF CORRECTION

Patent No. 4,287,221  Dated September 1, 1981

Inventor(s) Masayuki Tonedachi, et al

It is certified that error appears in the above-identified patent and that said Letters Patent are hereby corrected as shown below:

Column 6, line 6, change "hydroxpropylmethylcellulose" to --hydroxypropylmethylcellulose--;

lines 6/7, change "phtalate" to --phthalate--;

line 9, before "amount" insert --in an--.

Signed and Sealed this

Twenty-ninth Day of December 1981

[SEAL]

Attest:

Attesting Officer

GERALD J. MOSSINGHOFF

Commissioner of Patents and Trademarks